US00PP09627P

United States Patent [19]

Devroe

[11] Patent Number: Plant 9,627

[45] Date of Patent: Aug. 13, 1996

[54] *NEOREGELIA CAROLINAE* PLANT NAMED 'GRUVROE'

[75] Inventor: Luc J. Devroe, Lochristi, Belgium

[73] Assignee: Reginald Deroose, Evergem, Belgium

[21] Appl. No.: 374,298

[22] Filed: Jan. 18, 1995

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 3,971 11/1976 DeCoster et al. ..... Plt./88.8

P.P. 7,713 11/1991 Kuipers ..... Plt./88.8

*Primary Examiner*—James R. Feyrer

*Attorney, Agent, or Firm*—Foley & Lardner

[57] ABSTRACT

A new and distinct cultivar of *Neoregelia carolinae* plant named Gruvroe, characterized by its rosette form and larger plant habit; long leaves which are strongly curved at the base, straight in the middle, and curved down at the ends; variegated leaves having a yellow center with very thin green stripes or striations and dark green margins approximately 8 mm in width, and its socket which is formed with short, wide dark red to purple leaves, with light purple flowers being formed in the middle of the socket.

1 Drawing Sheet

The present invention comprises a new and distinct cultivar of Neoregelia plant, botanically known as *Neoregelia carolinae,* and referred to by the name Gruvroe.

The new cultivar is a mutation of the cultivar Perfecta Tricolor, disclosed in U.S. Plant pat. No. 3,971. The new cultivar was discovered by inventor Luc Devroe in 1985 in a greenhouse in Lochristi, Belgium growing among plants of the parent cultivar. The mutation was recognized due to its totally different leaf color and marking.

Subsequent asexual reproduction of the new cultivar by the inventor in Lochristi, Belgium, by taking shoots of the newly discovered plant, has demonstrated that the combination of characteristics as herein disclosed for the new cultivar are firmly fixed and are retained through successive generations of asexual reproduction.

The following traits have been repeatedly observed and in combination distinguish Gruvroe as a new and distict cultivar:

1. The plant is large and rosette in form.
2. Gruvroe has about 40 leaves and is approximately 50 to 70 cm in overall diameter when fully grown.
3. The leaves are strongly curved at the base, are then straight and a little erect, and then bend down at the ends.
4. The leaves are long (about 30 cm) and about 5.5 cm wide. The margin is finely prickly.
5. The leaves are variegated, with the middle being light yellow with very thin green stripes, and the margins (8 mm) dark green.
6. The socket is formed with short, very wide leaves in dark red to purple. The outer leaf margins and tips are dark green. Small light purple flowers are formed in the middle of the socket.

When comparing Gruvroe with the parent cultivar Perfecta Tricolor, similar characteristics are shape and color of the inflorescence, and the general outlook of the plants. The differences are numerous. Gruvroe is a bigger plant and its leaves do not bend down as much as the leaves of Perfecta Tricolor. Further, in the variegated leaves of Gruvroe, the center is a deeper yellow center are thinner. Still further, the socket is somewhat larger.

Compared to Devroe, disclosed in U.S. Plant Pat. No. 7,713, Gruvroe when grown under similar conditions has a substantially narrower green bands or striations, thereby giving the leaf interior a substantially yellow overall appearance. In addition, the leaves forming the rosette in Gruvroe are a much darker, cardinal red compared to the lighter cherry red rosette leaves of Devroe. Also, the flower head of Devroe is larger and extends higher in the plant.

When compared to Flandria, an unpatented cultivar which is the parent of Devroe, there are major differences, including plant habit and leaf color. Gruroe has a much more erect and full growth habit, and its leaf color is completely dissimilar to Flandria in which the leaf margins are very light yellow and the interior almost a solid green.

In the accompanying color photographic drawing, the photograph at the top of the sheet is a top perspective view showing the leaves and inflorescence of a typical potted plant of Gruvroe. The photograph at the bottom of the sheet is similar but somewhat enlarged to show the inflorescence in more detail. Colors are depicted as accurately as possible with color reproductions of this type.

The following obervations, measurements and values describe plants grown in Lochristi, Belgium under greenhouse conditions which closely approximate those generally used in horticultural practice. Color references are made to The Royal Horticultural Society (R.H.S.) Colour Chart, except where general color terms of ordinary significance are used. the color values were determined between 9.30 and 10.30 a.m. on Jun. 14, 1994 under bright and sunny daylight conditions in Lochristi, Belgium.

Classification:

*Botanical.*—*Neoregelia carolinae* cv Gruvroe.

*Commercial.*—Neoregelia Gruvroe.

Parentage: A spontaneous mutation of the parent Perfecta Tricolor.

Propagation: Asexual propagation by offshoots.

Plant: About 20 cm tall and 50 to 70, cm in overall diameter when fully grown (in a 12 cm pot). The leaves are strongly curved at the base, then straight and a little erect, and then bend down at the ends. The new cultivar has an excellent growth habit and is very vigorous.

Leaves:

*Shape.*—Oblong with tips bending down.

*Size.*—Length is approximately 30 cm. The width at the middle is 3.5 to 4.5 l cm and at the tip is 1.5 cm. The dark green margins are approximately 8 mm in width.

*Margin.*—Prickly.

*Surface texture.*—Mainly palisade parenchyma and spongy parenchyma.

*Veins or ribs.*—Slightly visible.

*Color (R.H.S.).*—Upper surface: Margin is closest to 147A but slightly darker. The interior leaf color is yellow 3C-D with a few very thin stripes which are 147A in color. Lower surface: Generally similar in color.

Rosette:

*Leaves forming the socket.*—Very short and about 5 cm wide.

*Color.*—Dark red to purple 53B-C but slightly more purple. The outer leaf margins and tips are dark green.

*Flowers.*—Arrangement: Small flower head. Color: Light purple 76A but slightly darker with a lighter edge. Fruit: Insignificant. Duration of the flowers: 2 to 3 months.

Reproductive organs:

*Stamens.*—Filaments: White. Anthers: Light yellow.

*Pistils.*—Stigma: White. Style: White. Ovary: White.

Disease resistance: No disease problems noted to date.

It is claimed:

1. A new and distinct cultivar of *Neoregelia carolinae* plant named Gruvroe, as illustrated and described.

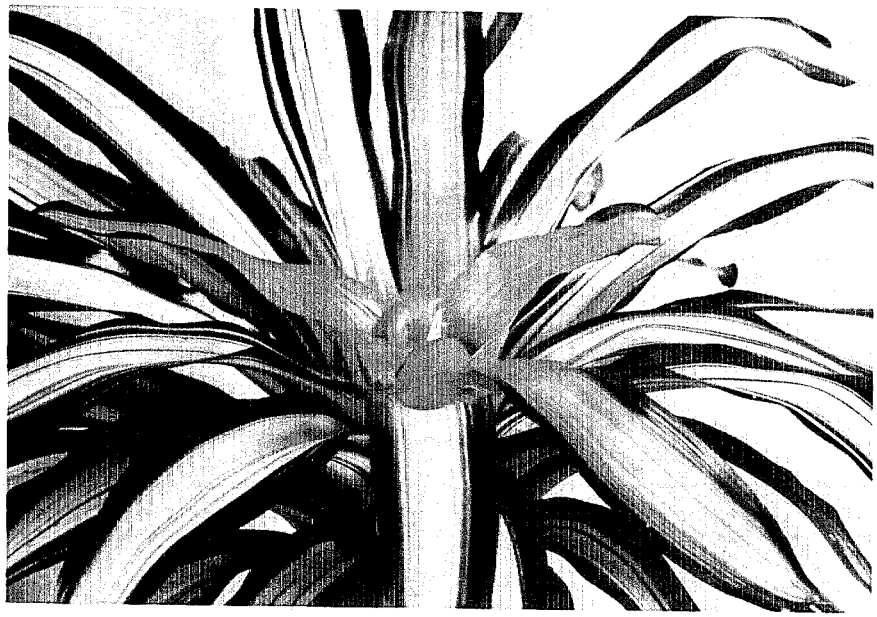
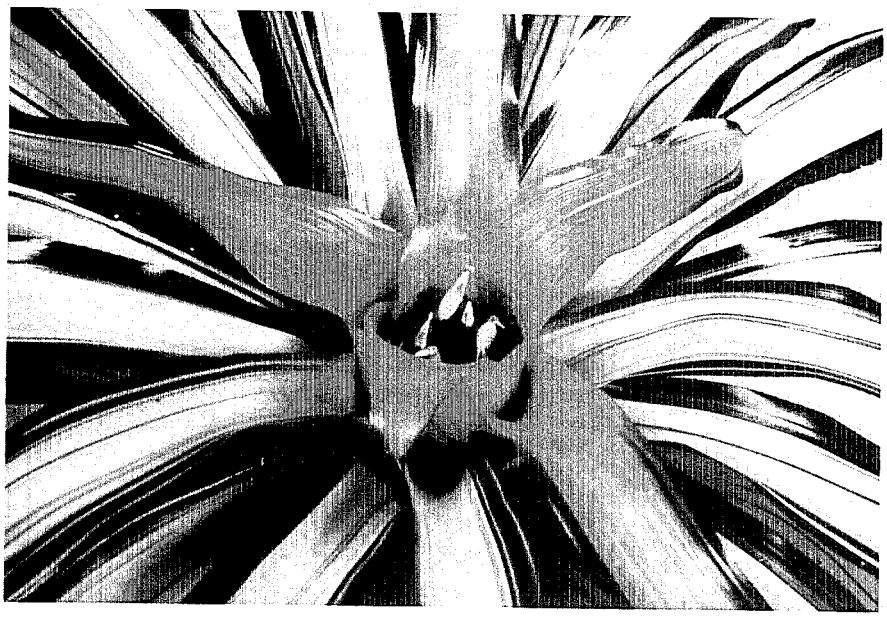

* * * * *